US010363439B2

(12) United States Patent
Amaldi

(10) Patent No.: US 10,363,439 B2
(45) Date of Patent: Jul. 30, 2019

(54) ION ACCELERATION COMPLEX FOR THE TREATMENT OF ATRIAL FIBRILLATIONS

(71) Applicant: Ugo Amaldi, Geneva (CH)

(72) Inventor: Ugo Amaldi, Geneva (CH)

(73) Assignee: FONDAZIONE PER ADROTERAPIA ONCOLOGICA—TERA, Novara (IT)

( * ) Notice: Subject to any disclaimer, the term of this patent is extended or adjusted under 35 U.S.C. 154(b) by 20 days.

(21) Appl. No.: 14/464,148

(22) Filed: Aug. 20, 2014

(65) Prior Publication Data

US 2015/0057484 A1    Feb. 26, 2015

(30) Foreign Application Priority Data

Aug. 22, 2013   (IT) ................. CO2013A0036

(51) Int. Cl.
*A61N 5/10* (2006.01)
*H05H 7/22* (2006.01)
*H05H 9/04* (2006.01)

(52) U.S. Cl.
CPC ......... *A61N 5/1064* (2013.01); *A61N 5/1067* (2013.01); *H05H 7/22* (2013.01); *H05H 9/041* (2013.01); *A61N 2005/1087* (2013.01); *H05H 2277/11* (2013.01)

(58) Field of Classification Search
None
See application file for complete search history.

(56) References Cited

U.S. PATENT DOCUMENTS

| 6,888,326 | B2 * | 5/2005 | Amaldi ........... H05H 7/22 313/359.1 |
| 7,423,278 | B2 | 9/2008 | Amaldi et al. |
| 7,554,275 | B2 | 6/2009 | Amaldi |
| 8,405,056 | B2 | 3/2013 | Amaldi et al. |
| 2006/0170381 | A1 | 8/2006 | Amaldi et al. |

(Continued)

FOREIGN PATENT DOCUMENTS

| EP | 2 106 678 B1 | 10/2009 |
| WO | 2008/081480 A1 | 7/2008 |
| WO | 2008/086434 A2 | 7/2008 |

OTHER PUBLICATIONS

Degiovanni et al., Design of a Fast-Cycling High-Gradient Rotating Linac for Protontherapy, Proceedings of IPAC 2013, Jun. 2013.*

(Continued)

*Primary Examiner* — James Choi
(74) *Attorney, Agent, or Firm* — Young & Thompson

(57) ABSTRACT

A system (12) is proposed for the acceleration of ions to treat Atrial Fibrillation (AF), arteriovenous malformations (AVMS) and focal epileptic lesions; this system (12) includes a pulsed ion source (1), a pre-accelerator (3) and one or more linear accelerators or linacs (5, 6, 7) operating at frequencies above 1 GHz with a repetition rate between 1 Hz and 500 Hz. The particle beam coming out of the complex (12) can vary (i) in intensity, (ii) in deposition depth and (iii) transversally with respect to the central beam direction. The possibility of adjusting in a few milliseconds and in three orthogonal directions, the location of each energy deposition in the body of the patient makes that system of accelerators (12) perfectly suited to irradiation of a beating heart.

11 Claims, 1 Drawing Sheet

(56) References Cited

U.S. PATENT DOCUMENTS

| | | | | |
|---|---|---|---|---|
| 2009/0180589 A1* | 7/2009 | Wang | ............... | A61N 5/10 378/65 |
| 2010/0320403 A1* | 12/2010 | Amaldi | ............... | A61N 5/10 250/492.3 |
| 2013/0092839 A1* | 4/2013 | Kraft | ............... | A61N 5/1043 250/360.1 |

OTHER PUBLICATIONS

Fuchs et al., A pencil beam algorithm for helium ion beam therapy, Medical Physics 39, 6726 (2012).*

Jones et al., Design of a Beam Transport System for a Proton Radiation Therapy Facility, Proceedings of the 1999 Particle Accelerator Conference, New York, 1999.*

Quigg et al., Stereotactic Radiosurgery for Treatment of Epilepsy, Arch Neurol / vol. 65 (No. 2), Feb 2008.*

A.Degiovanni et al.: "Design of a Fast-Cycling High-Gradient Rotating Linac for Protontherapy", Proceedings of IPAC 2013, Jun. 2013 (Jun. 2013), pp. 3642-3644, XP002724134, abstract; figure 1, Introduction; p. 3642, col. 1, last paragraph; p. 3462, col. 2, Linac Layout; Beam Energy Modulation; Beam Line Design; p. 3643-3644.

IT Search Report, dated May 9, 2014, from corresponding IT application.

* cited by examiner

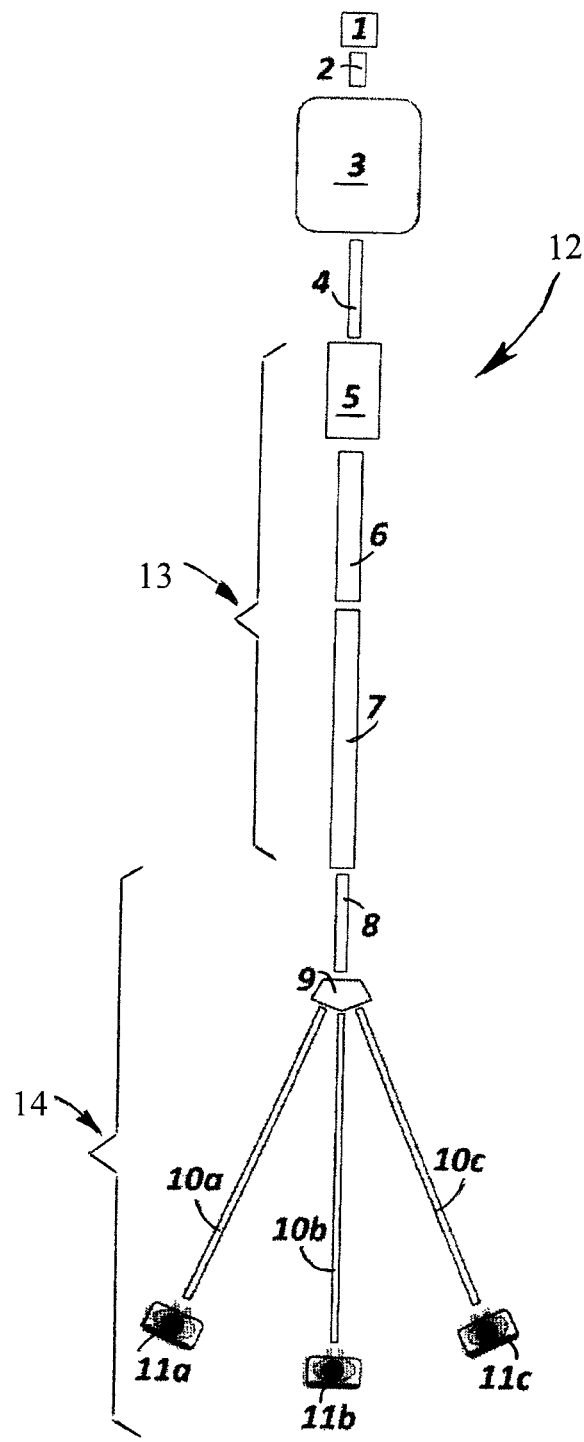

ION ACCELERATION COMPLEX FOR THE TREATMENT OF ATRIAL FIBRILLATIONS

DESCRIPTION OF THE INVENTION

Field of the Invention

The present invention concerns the use of linear ion accelerators (usually called "linacs") for the treatment of atrial fibrillation (AF) and ion accelerator system, or complex, there for according to the preambles of claims 1 and 2, whereas the treatment of atrial fibrillation takes place by means of the known "spot" scanning and the so-called "multi-painting" techniques. This accelerator complex is called LINAF.

Technological Background and Known Technique

It is well known that hadrontherapy is the modern cancer radiation therapy that uses beams either of protons or of heavier charged nuclear particles with atomic mass number larger than 1.

Few years ago it was suggested to use, with analogue techniques, the same beams to cure Atrial Fibrillation, with the limits and drawbacks indicated hereafter.

Atrial Fibrillation

In elderly people Atrial Fibrillation (AF) is the most common type of heart arrhythmia and a high risk factor for heart attack. The life-time risk to develop atrial fibrillation is 25%. Prevalence increases from 0.1%, among adults younger than 55 years, to 9.0% in persons aged 80 years or older. The median age of persons with atrial fibrillation is 67 years for men and 75 years for women and—on average—about 1% of the overall population suffers with atrial fibrillation. It is predicted that this percentage will increase 2.5-fold during the next 50 years, reflecting the growing proportion of elderly individuals.

In the United States, about 3 million people per year experience an AF episode and approximately 20% of all strokes (75,000/y) can be attributed to AF; the overall cost of treatment of AF is about 7 billion dollars per year. In Europe the corresponding cost is about 1% of the annual healthcare expenditure. Current AF treatment options are: medicines to control atrial fibrillation, medicines to reduce the risk of a stroke, cardio-version (electric shock treatment), catheter ablation and having a pace maker fitted.

Catheter ablation interrupts abnormal electrical circuits in the heart. Catheters are guided, through the patient's veins, into the heart where they record electrical activity. When the source of the abnormality is found, an energy source (such as for example high-frequency radio-waves that generate heat) is transmitted through one of the catheters to destroy the tissue.

This technique is invasive and refused by many patients.

According to the inventor, the recently proposed use of beams of charged hadrons to destroy the dangerous electrical connections in the heart, could be a valuable non-invasive alternative. Moreover, it would be applied without anaesthesia and the patient would not feel anything, as is the case during a standard radiotherapy session. Relevant papers in the field are:

Ch. Bert, R. Engenhart-Cabillic, and M. Durante, *Particle therapy for non-cancer diseases*, Med. Phys. 39 (2012) 1716.

A. Constantinescu, H. I. Lehmann, C. Graeff, D. Packer, M. Durante, and C. Bert, *Influence of cardiac motion on pulmonary veins for the non-invasive treatment of atrial fibrillation with a scanned carbon ion beam*, GSI Scientific Report 2012, p. 472.

The use of hadron beams for the treatment of AF is, according to the inventor, a novel technique, based on a skilful development of the technique based on X ray beams discussed, for instance, in:

A. Sharma, D. Wong, G. Weidlich, T. Fogarty, A. Jack, T. Sumanaweera, and P. Maguire, *Non-invasive stereotactic radiosurgery (CyberHeart) for creation of ablation lesions in the atrium*, Heart Rhythm 7 (2010) 802.

R. M. Sullivan and A. Mazur, *Stereotactic robotic radiosurgery (CyberHeart): A cyber revolution in cardiac ablation?* Heart Rhythm 7 (2010) 811.

It can also be noticed that hadrons are definitely to be preferred to X rays because of the much better localization of the delivered dose due to the Bragg peak, in which—at the end of the charged particle range—the maximum energy density is deposited in the patient's body; this is the same property for which protons are better than X rays in the treatment of solid cancers that are close to critical organs.

In the on-going preliminary studies of this new technique the dose is given with sub-millimeter precision by "painting" with the Bragg "spot" the relevant target tissues of the pulsing heart. In doing so, it is necessary to rapidly vary—before sending every spot—its two transverse positions and also its depth in the body so as to compensate for the movements due to (i) the respiration cycle and (ii) the patient's heartbeat.

Therefore any optimal future treatment will have to include a three-dimensional feedback system, to reduce unwanted irradiations of the surrounding healthy tissues limiting the dose to the concerned target and to treat the patient in a short time.

In the opinion of many experts studying this new technique, carbon ions are to be preferred to protons because they have three times less multiple scattering and less straggling, so that the spot covers a volume that is about ten times smaller. However, the needed accelerator is much larger because—for the same penetration in the patient body—the magnetic rigidity of carbon ions is three times larger than the magnetic rigidity of the corresponding proton beam.

It can furthermore be observed that in the field of cancer therapy with hadron beams, two types of accelerators are used: cyclotrons (isochronous or synchrocyclotrons; conventional or superconducting) and synchrotrons. Several companies offer turnkey centres for proton and/or carbon ion therapy based on such accelerators. These are the accelerators that the scientists, who are pioneering the use of proton and ions in the treatment of AF, use and are planning to use.

The Inventor has already proposed linear accelerators (linacs) for both proton and light ion cancer therapy:

1) U.S. Pat. No. 6,888,326 B2 "Linac for Ion Beam Acceleration, U. Amaldi, M. Crescenti, R. Zennaro.
2) U.S. Pat. No. 7,554,275 B2 "Proton Accelerator Complex for Radio-isotopes and Therapy, U. Amaldi.
3) European Patent EP 2 106 678 B1 "Ion Accelerator System for Hadrontherapy, Inventors: U. Amaldi, S. Braccini, G. Magrin, P. Pearce, R. Zennaro.
4) U.S. Pat. No. 8,405,056 B2 "Ion Accelerator System for Hadrontherapy, Inventors: U. Amaldi, S. Braccini, G. Magrin, P. Pearce, R. Zennaro.

Similar linacs have many advantages in cancer therapy. The Inventor has now surprisingly pointed out that these linacs offer advantages also in the new developments concerning AF treatment.

SUMMARY OF THE INVENTION

The main aim of the present invention is to propose an application of ion linear accelerators (linac) for the treatment of Atrial Fibrillation and the relevant ion accelerator system with charged particles that do not present the limits and disadvantages of the known techniques; these systems, or complexes, are usefully known in part and are of compact and light execution, as well as requiring a small installation surface, so that the installation in hospital centres is made easier. The linac for the treatment of atrial fibrillation has been called "LINAF".

This aim is reached in its different aspects with the application of linear ion accelerators (or linacs) for the treatments of Atrial fibrillation and the corresponding ion accelerator system having the features of Claims 1 and 2. Further developments are inferable from the dependent claims.

With the use of linear ion accelerators for the treatment of atrial fibrillation and of the corresponding devices for its realisation, according to the invention several and important advantages can be achieved, which are discussed in what follows, together with the different aspects of the invention.

According to the invention the proposed systems are based on hadron linacs working at high frequencies and high gradients; they are made of many "accelerating units" powered separately. Such linacs can accelerate any type of ion.

Within the present invention the inventor has further pointed out that helium ions are particularly interesting because they require, in order to be accelerated, a much shorter linac with respect to carbon ions, while they produce spots having transversal and longitudinal smaller sizes by a factor two compared to the spots of a proton beam, which deposits the same dose at the same depth in the patient's body.

To meet the needs described above, according to the present invention, ions—in particular helium ions—are accelerated to the energy needed for AF treatments by one or more linac section(s) running at high-frequency—i.e. at frequencies larger than 1 GHz. The typical maximal kinetic energies are the ones corresponding to an ion range of 180 mm in water: 160 MeV for protons, 640 MeV (160 MeV/u) for helium ions and 3600 MeV (300 MeV/u) for carbon ions. The corresponding integrals of the accelerating electric field are 160 MV, 320 MV and 600 MV.

High-frequency ion linacs can run with large accelerating gradients (up to 40-50 MV/m) and thus, to reach these energies accelerating structures of limited lengths are needed. However, these numbers immediately show that a helium ion linac for AF is about twice longer than a proton linac and a carbon ion linac is about twice longer than a helium ion linac.

The injector of the high-frequency linac (named here "pre-accelerator") can be either a linea accelerator, specific for low-speed ions, or a circular accelerator (cyclotron, synchrocyclotron, FFAG or other) or else a combination of two or more of these well-known accelerators.

The output beam of the linac for AF is pulsed and the pulses are 3-5 microsecond long: they follow one other at a repetition rate that varies—according to the needs—between 1 Hz and 500 Hz.

In the final linac, the energy (and thus the deposition depth) of every spot can be adjusted by switching off a number of units and by varying the power and the phase of the radiofrequency power pulses sent to the last active units. Thus the linacs the ideal accelerator for an 'active' dose spreading system: the ion energy and the number of ions of a pulse can be adjusted, electronically and in a few milliseconds, from pulse to pulse. The energy is adjusted by acting on the power pulses and their phases—sent to the accelerating units—, as said above, while the number of ions is usually adjusted by acting on the electrostatic lenses of the particle source, which, as said, produces 3-5 microsecond long pulses at a repetition rate between 1 Hz and 500 Hz.

Moreover, given the high repetition rate, every "voxel" of the target tissue can be visited at least ten times in the treatment mode that is often called "multi-painting".

The AF optimal treatment is obtained, according to the invention, by combining multi-painting with a three-dimensional feedback system.

It has to be stressed that in a cyclotron the adjustment of the energy is obtained by the mechanical movement of appropriate absorbers, which causes the unwanted activation of surrounding material and, usually, requires more than 10 meters of magnets to "clean" the beam downstream of the absorbers. Moreover the adjustment of such absorbers requires typically 100 milliseconds. The fast electronic three-dimensional adjustment of the spot position is not feasible with a conventional synchrotron, since the energy is usually varied every cycle of acceleration basis, i.e. typically every one or two seconds.

Overall, a high-frequency linac is superior to all other accelerators because the beam energy can be varied from pulse to pulse (i.e. every few milliseconds) together with the number of particles to be delivered to the tumour target (which is set by acting on the very low energy particle source).

The time and intensity structure of the high repetition rate pulsed beam is particularly suited for the dose delivery in AF treatments, since it improves, with "multi-painting", the technique of 'spot scanning' in use at the PSI Centre, Paul Scherrer Institute, Villigen, Switzerland (E. Pedroni et al, *The 200 MeV proton therapy project at the Paul Scherrer Institute: conceptual design and practical realisation*, Medical Physics, 22(1), (1995) 37).

In addition to the optimal time and intensity structure of the ion beam, the use of high-gradient ion linacs according to the invention presents other advantages.

First of all the accelerator is lighter, easier to be carried and install with respect to existing cyclotrons and synchrotrons, and is characterized by a modular structure composed of the same high-tech units repeated almost without variation for each accelerating module. Secondly, the proposed system is compact, so minimal volumes and installation surfaces are needed, therefore the installation in hospital centres is made easy.

Moreover, the high frequency of the linac implies low power consumptions, which reflects in reduced exploitation costs.

In summary, with respect to the other hadron accelerators, which can be used for AF treatments, the present invention allows to build a compact low-power consumption complex, or facility, which delivers the dose with a three-dimensional spot scanning technique with multi-painting and feedback to compensate for the movements of the irradiated heart.

According to another aspect of the invention, this accelerator complex can also be used to treat arteriovenous malformations (AVMs) and focal epileptic lesions, which can be irradiated with beams of protons (and other ions) a subject discussed in F. J. A. I. Vernimmen et al., *Stereotactic proton beam therapy for intracranial arteriovenous malformations*, Int J RadiatOncolBiolPhys 62 (2005) 44, and in M. Quigg et al., *Radiosurgery for epilepsy: clinical experience and potential antiepileptic mechanisms*, Epilepsia 53 (2012) 7.

BRIEF DESCRIPTION OF THE DRAWING

Further advantages, details and characteristics of the use of linear ion accelerations for the treatment of Atrial Fibrillation and the corresponding ion accelerator system according to the invention result from the following description of the proposed application and of a from of implementation of an appropriate ion accelerator system schematically illustrated as an example in the annexed drawing.

With reference in the first place to the only FIGURE, the main components of the complex of hadron accelerators for the application of the invention are:
1. An ion source, producing ion pulses about 5 microsecond long at repetition rates in the range between 1 Hz and 500 Hz;
2. A Low Energy Beam Transport magnetic channel (LEBT—Low Energy Beam Transport);
3. A pre-accelerator, which can be either a Radiofrequency Quadrupole (RFQ) or a cyclotron or a synchrocyclotron or a special type of linac capable of accelerating very slow hadrons;
4. A Medium Energy Beam Transport channel (MEBT);
5. A first linac section, at a radiofrequency greater than 1 GHz;
6. A second linac section working at a radiofrequency that can be a multiple of the one of the first linac section;
7. A third linac section at a frequency that can be a multiple of the one of the second linac section;
8. A High Energy Beam Transport channel (HEBT) that brings the accelerated beam to the patient treatment rooms;
9. A fan-out magnet that, in its preferred implementation, sends the beam pulses, of variable energy and intensity, to the treatment rooms;
10. A system of beam transport lines to wards the treatment rooms, each containing the two scanning magnets (that define the dimensions of the irradiated field by moving vertically and horizontally the ion beam) and the monitoring system;
11. Robotic chairs where the seated patients receive in the heart the dose prescribed by the Treatment Planning System (TPS).
12. The facility or complex of hadron accelerators according to the invention;
13. A complex of subsystems or sections of linac (5; 6; 7);
14. A system of transport lines of the pulses of ions to the points where patients are irradiated.

It is worth underlining that the subsystems or sections 5,6 and 7 of the FIGURE are not necessarily all present at the same time in each implementation.

More precisely, referring to FIG. 1, according to the invention the hadron accelerator complex 12 includes various kinds of accelerators serially connected, namely a pre-accelerator 3 and a number of linac sections 5, 6, 7; their oscillatory frequencies can gradually increase so as to have in the last linac a higher gradient and thus reduce the overall length of the system. To simplify the overall scheme some of the three linac sections 5,6, 7 may be absent.

The pre-accelerator 3 is fed by the ion source 1. Its output beam can be continuous or, better, modulated at the 1-500 Hz repetition rate in pulses that are few microseconds long, so that the number of ions sent through MEBT 4 to the first section of the linac 5 is minimal and does not produce unnecessary radioactivity in the elements which follow.

Each linac section 5,6,7 is made of 'accelerating units', which can be either Travelling Wave linacs or Standing Wave linacs and have structures of the types Drift Tube Linac (DTL), IH Drift Tube Linac, CH Drift Tube Linac, Coupled-cavity LinacUSing Transverse Electric Radial fields (CLUSTER), Side Coupled Drift Tube Linac (SCDTL), Cell Coupled Linac (CCL) or others according to the speed of the accelerated hadrons. Accelerating structures of these types are well known, others are described in the documents U.S. Pat. No. 6,888,326 B2, U.S. Pat. No. 7,423,278 B2 and U.S. Pat. No. 7,554,275 B2 in the name of the Applicant and are quoted and incorporated in the present application as examples, referring to the quoted documents for further details.

It can be remarked that to reach, with an average gradient equal to 30 MV/m, the total voltage required for AV treatments—protons: about 160 MV; helium ions: about 320 MV; carbon ions: about 600 MV—the total lengths of the linacs are about 5 m for protons, 10 m for helium ions and 20 m for carbon ions.

In general the linac section producing the largest acceleration gradient is the one indicated as 7 in FIG. 1. As described above, it is this last section that is usually subdivided in units that are independently powered so that the energy of the output particles can be adjusted pulse by pulse.

The accelerated ion beam is transported to the treatment rooms through the HEBT channel 8. In some forms of implementation this is obtained with the fan-out magnet 9, whereas in other implementations the standard beam transport design—as used in cancer therapy centres featuring rotating gantries—will be chosen.

Patients can be treated either on a robotic chair 11, as indicated in the preferred implementation of the picture, or lying on a computer controlled moving couch.

In the application for the treatment of Atrial Fibrillation according to the invention the particle beam coming out of complex 12, 8 can vary in (i) intensity (acting on the ion source (1)), (ii) in deposition depth (by adjusting independently the radiofrequency power sources feeding the accelerating units of the linacs), and (iii) transversally with respect to the central beam direction (by varying the currents in the coils of two orthogonal scanning magnets placed upstream of each patient).

The possibility to adjust, in a few milliseconds and in three orthogonal directions, the location of each energy deposition in the body of the patient makes the accelerator system 12 perfectly suited to irradiation of a beating heart.

As an example a possible scheme of said complex 12, summarized in the following Table 1, is composed of:
(A) a computer controlled helium source 1—which can be either of the Electron Cyclotron Resonance (ECR) type (properly modified to obtain a beam pulsed at repetition rates in the range 1-500 Hz), or of the Electron Beam Ion Source type (EBIS) or other;
(B) a60 MeV/u cyclotron or synchrocyclotron 3, with coils which are either at room temperature or superconducting;
(C) a Cell Coupled Linac of the LIBO 7 type running at 3 GHz and made of 10 separately powered units.

The firms Thales, France and CPI, US produce—among other companies—the 3 GHz klystrons needed for the form of implementation mentioned.

In the form of the preferred implementation of the linac in table 1, the pre-accelerator is superconducting. Its magnetic field configuration and dimensions are similar to the ones of the superconducting cyclotron commercialized by Varian Medical Systems, Inc. (Palo Alto, USA) for cancer proton beam therapy. The magnet, requiring only about 40 kW for cryogenics, has a diameter of 3.2 m and a height of 1.6 m. The overall consumption is below 200 kW. The source 1 injects axially the pulses of helium ions.

TABLE 1

Example of a 3 GHz linac to accelerate 4He2+ions

| | |
|---|---|
| Frequency [MHz] | 2998 |
| Q (ion charge) | 2 |
| A (ion mass number) | 4 |
| Input energy [MeV/u] | 60 |
| Total input energy [MeV] | 240 |
| Maximum output energy [MeV/u] | 160 |
| Total maximum output energy [MeV] | 640 |
| Number of accelerating cells per accelerating structure (tank) | 18-16 |
| Diameter of the iris [mm] | 7 |
| Number of units | 10 |
| Lengths of the units [m] | 0.75-1.05 |
| Total length of the Linac [m] | 9.5 |
| Average transit time factor T | 0.85 |
| Effective Shunt Impedance ZT2 [MΩ/m] | 53-77 |
| Average electric field on the axis E0 [MV/m] | 33 |
| Maximum surface electric field [MV/m] | 140 |
| Normalized transverse acceptance at 2 rms [π mm mrad] | 2.4 |
| Peak power per unit [MW] | 10 |
| Duration of RF pulse [μs] | 4 |
| Repetition rate [Hz] | 120 |
| Fraction of time with beam ('duty cycle') [%] | 0.048 |
| Average power to feed the 10 klystrons [kW] | 150 |

From the structural and functional description of the various forms of implementations of ion acceleration plants or complexes for application, according to the invention, in the treatment of atrial fibrillation, it can be noticed that the proposed invention efficiently achieves the stated aim and obtains the mentioned advantages.

The experts in the field may introduce modifications and variations of the single components and their combination, both in structure and/or dimensions, of the systems proposed for the use following the invention by adapting it to specific cases without departing from the scope of the present invention as described in the following claims.

LITERATURE

List of some publications in the field of high-frequency linacs for hadrontherapy:

R. W. Hamm, K. R. Crandall, and J. M. Potter, *Preliminary design of a dedicated proton therapy linac*, in Proc. PAC90, Vol 4 (San Francisco, 1991) 2583.

U. Amaldi, M. Grandolfo and L. Picardi (Eds), *The RITA Network and the Design of Compact Proton Accelerators*, INFN, Frascati, 1996, ISBN 88-86409-08-7. The "Green Book", Chapter 9.

L. Picardi, C. Ronsivalle and B. Spataro, *Design development of the SCDTL structure for the TOP Linac*, Nuclear Instruments and Methods A, 425 (1999) 8.

U. Amaldi et al., *A Linac-booster for Protontherapy: Construction and Tests of a Prototype*, Nuclear Instruments and Methods A 521 (2004) 512.

U. Amaldi, S. Braccini, and P. Puggioni, *High frequency linacs for hadrontherapy*, Rev. Acc. Sci. Tech. 2 (2009) 111.

U. Amaldi et al., *Accelerators for hadrontherapy: from Lawrence cyclotrons to linacs*, Nuclear Instruments and Methods A620 (2010) 563.

C. De Martinis et al., *Acceleration tests of a 3 GHz proton linear accelerator (LIBO) for hadrontherapy*, Nuclear Instruments and Methods A 681 (2012) 10.

The invention claimed is:

1. An accelerator complex (12) comprising:
   an ion source (1) configured for producing beam pulses of ions with an atomic number between 1 (protons) and 10 (neon ions),
   a pre-accelerator (3) configured for accelerating rates of the beam pulses,
   a high-energy section (13) configured to receive beam pulses from the pre-accelerator (3), the high-energy section (13) containing at least one linac (5; 6; 7) comprising a plurality of units and configured to:
   (i) run at a frequency larger than 1 GHz with a repetition rate between 10 Hz and 400 Hz, and
   (ii) vary energy of outgoing accelerated ions by acting on the radiofrequency sources of at least one linac (7) to switch off a number of units, and to vary the power and the phase of the radiofrequency power pulses sent to the final active units of a last section of the linac,
   said outgoing accelerated ions of beam pulses forming a spot that deliver a dose of beam pulses to a target area of a patient's body,
   a three-dimensional feedback system configured to vary, before sending every spot, two transverse positions and a depth in the patient's body so as to compensate for the movements of a targeted area such that the dose of beam pulses delivered by every spot is limited to a targeted area in order to reduce unwanted irradiation to non-targeted areas, and
   a High Energy Beam Transport channel (HEBT) with an associated magnet system that transports the beam pulses forming every spot from the high-energy section (13) to a treatment room of said patient,
   wherein the configuration of the units and the configuration of the three-dimensional feedback system is such that the variation of the depth by the three-dimensional feedback system corresponds to the variation of energy of outgoing accelerated ions.

2. The complex for ion acceleration (12) according to claim 1, wherein the high-energy section (13) contains two or three linac section(s) and one or more linac sections (5; 6; 7) run at different frequencies.

3. The complex for ion acceleration (12) according to claim 1, wherein the complex comprises more than one pre-accelerator (3) configured for accelerating rates of the beam pulses.

4. The complex for ion acceleration (12) according to claim 1, wherein the pre-accelerator (3) is a room temperature, a superconducting Linac, or a Radio Frequency Quadrupole (RFQ).

5. The complex for ion acceleration (12) according to claim 1, wherein the pre-accelerator (3) is a room temperature, a superconducting cyclotron/synchrocyclotron, or a FFAG accelerator.

6. The complex for ion acceleration (12) according to claim 1, wherein the ion source (1) is computer controlled so as to adjust the dose delivered in every single spot.

7. The complex for ion acceleration (12) according to claim 1, wherein the complex comprises an associated layout (14) of pulse beam transport to rooms, robotic chairs, or beds other locations (11a, 11b, 11 c) for treatment of patients in a computer controlled manner, the associated layout (14) includes a magnet fan-out (9) with associated intermediate beam transport lines (10a, 10b, 10 c), each intermediate beam transport line having two magnets configured for transverse scanning and a monitoring system.

8. The complex for ion acceleration (12) according to claim 1, wherein the linac (5; 6; 7) is a 3 GHz linac that is configured to accelerate 4He2+ ions and is configured to operate with the following parameters:

| | |
|---|---|
| Frequency [MHz] | 2998 |
| Q (ion charge) | 2 |
| A (ion mass number) | 4 |
| Input energy [MeV/u] | 60 |
| Total input energy [MeV] | 240 |
| Maximum output energy [MeV/u] | 160 |
| Maximum total output energy [MeV] | 640 |
| Number of cells in an accelerating structure (or tank) | 18-16 |
| Iris diameter [mm] | 7 |
| Number of units | 10 |
| Unit length [m] | 0.75-1.05 |
| Total length of the linac [m] | 9.5 |
| Average transit time factor T | 0.85 |
| Effective Shunt Impedance's = $ZT^2$ [MΩ/m] | 53-77 |
| Average electric field on the axis E0 [MV/m] | 33 |
| Maximum surface electric field [MV/m] | 140 |
| Transverse normalized acceptance at 2 rms [π mm mrad] | 2.4 |
| Peak power per unit [MW] | 10 |
| RF Pulse duration [µs] | 4 |
| Repetition rate [Hz] | 120 |
| Fraction of time with beam (or duty cycle) [%] | 0.048 |
| Average power to feed the 10 klystrons [kW] | 150. |

9. A method for the treatment of atrial fibrillation by spot scanning and multi-painting technique, comprising administering to a patient in need thereof accelerated ions from an accelerator complex according to claim 1, wherein a three-dimensional feedback system is foreseen to treat the patient without unwanted irradiation of the tissues that need to be spared.

10. A method for the treatment of arteriovenous malformations (AVMs) and focal epileptic lesions, comprising administering to a patient in need thereof accelerated ions from an accelerator complex according to claim 1, wherein a three-dimensional feedback system is foreseen to treat the patient without unwanted irradiation of the tissues that need to be spared.

11. An accelerator complex (12) comprising:
an ion source (1) configured for producing beam pulses of ions with an atomic number between 1 (protons) and 10 (neon ions),
a pre-accelerator (3) configured for accelerating rates of the beam pulses,
a high-energy section (13) configured to receive beam pulses from the pre-accelerator (3), the high-energy section (13) containing at least one 3 GHz linac (5; 6; 7) that is configured to accelerate 4He2+ ions of beam pulses produced by said ion source (1) and to operate with the following parameters:

| | |
|---|---|
| Frequency [MHz] | 2998 |
| Q (ion charge) | 2 |
| A (ion mass number) | 4 |
| Input energy [MeV/u] | 60 |
| Total input energy [MeV] | 240 |
| Maximum output energy [MeV/u] | 160 |
| Maximum total output energy [MeV] | 640 |
| Number of cells in an accelerating structure (or tank) | 18-16 |
| Iris diameter [mm] | 7 |
| Number of units | 10 |
| Unit length [m] | 0.75-1.05 |
| Total length of the linac [m] | 9.5 |
| Average transit time factor T | 0.85 |
| Effective Shunt Impedance's = $ZT^2$ [MΩ/m] | 53-77 |
| Average electric field on axis E0 [MV/m] | 33 |
| Maximum surface electric field [MV/m] | 140 |
| Transverse normalized acceptance at 2 rms [π mm mrad] | 2.4 |
| Peak power per unit [MW] | 10 |
| RF Pulse duration [µs] | 4 |
| Repetition rate [Hz] | 120 |
| Fraction of time with beam (or duty cycle) [%] | 0.048 |
| Average power to feed the 10 klystron [kW], | 150 | the high-energy section (13) being configured to vary energy of outgoing accelerated 4He2+ ions by acting on the radio frequencies sources of at least one linac (7), said outgoing accelerated 4He2+ ions of beam pulses forming a spot that delivers a dose of beam pulses to a target area of a patient's body, a three-dimensional feedback system configured to vary, before sending every spot, two transverse positions and a depth in the patient's body so as to compensate for the movements of a targeted area such that the dose of beam pulses delivered by every spot is limited to a targeted area in order to reduce unwanted irradiation to non-targeted areas, and a High Energy Beam Transport channel (HEBT) with an associated magnet system that transports the beam pulses forming every spot from the high-energy section (13) to a treatment room of said patient.

\* \* \* \* \*